United States Patent [19]

Tsuk et al.

[11] 3,972,995
[45] Aug. 3, 1976

[54] DOSAGE FORM
[75] Inventors: Andrew G. Tsuk, Plattsburgh; Frederick H. Martin, West Chazy, both of N.Y.
[73] Assignee: American Home Products Corporation, New York, N.Y.
[22] Filed: Apr. 14, 1975
[21] Appl. No.: 567,788

[52] U.S. Cl................................ 424/28; 128/156; 128/260; 128/268
[51] Int. Cl.² ..................... A61F 7/02; A61L 15/03; A61M 35/00
[58] Field of Search .................. 424/28, 14, 15, 16; 128/268, 260, 156

[56] References Cited
UNITED STATES PATENTS

| 3,053,255 | 9/1962 | Meyer | 128/268 |
|---|---|---|---|
| 3,339,546 | 9/1967 | Chen | 128/156 |
| 3,429,308 | 2/1969 | Russell | 128/1 |
| 3,444,858 | 5/1969 | Russell | 128/260 |
| 3,598,123 | 8/1971 | Zaffaroni | 128/268 |
| 3,632,740 | 1/1972 | Robinson et al. | 424/28 |
| 3,731,683 | 5/1973 | Zaffaroni | 128/268 |
| 3,742,951 | 7/1973 | Zaffaroni | 128/268 |
| 3,797,494 | 3/1974 | Zaffaroni | 128/268 |
| 3,911,099 | 10/1975 | Defoney et al. | 424/28 |

Primary Examiner—Shep K. Rose

[57] ABSTRACT

The disclosure is directed to dosage forms for buccal administration of a drug and are directly applicable to the interior surfaces of the mouth. The dosage form is comprised of a support member, which is water insoluble, waterproof and flexible, a moisture activated, adhesive precursor applied to one surface of the support member and an active ingredient applied to the central portion of the support member either directly or dispersed in a matrix. In one embodiment, a recess is provided in the support member to receive the active ingredient. When the dosage form is applied directly to the interior surface of the mouth, contact with saliva activates the adhesive and causes the support member to adhere to the interior surface of the mouth, thereby exposing the active ingredient to a limited area of the oral mucosa while isolating the active ingredient from the remainder of the oral environment.

2 Claims, 8 Drawing Figures

U.S. Patent Aug. 3, 1976 Sheet 1 of 2 3,972,995
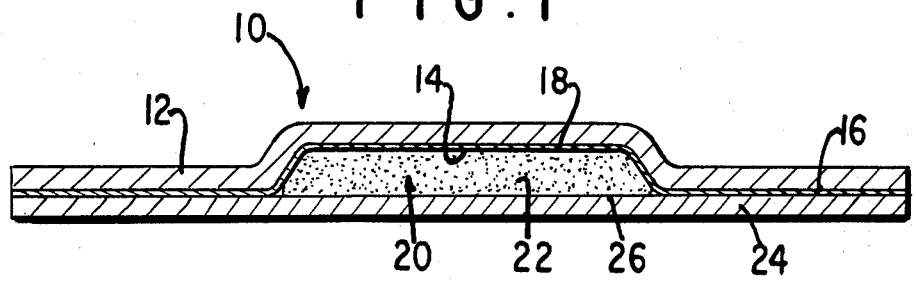
FIG.1
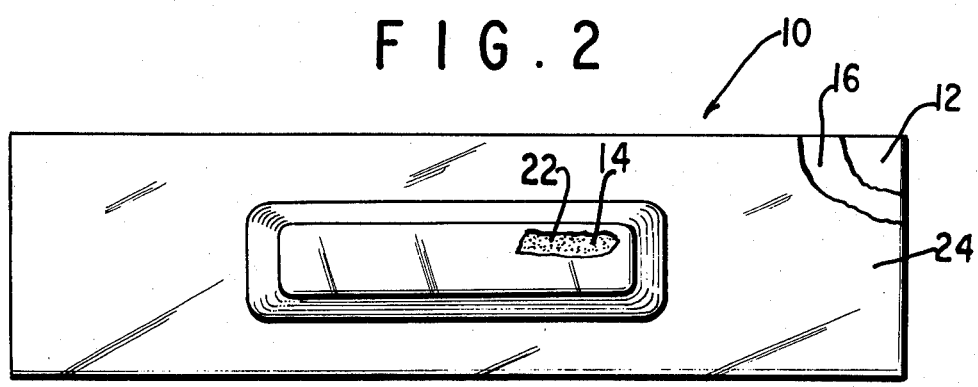
FIG.2
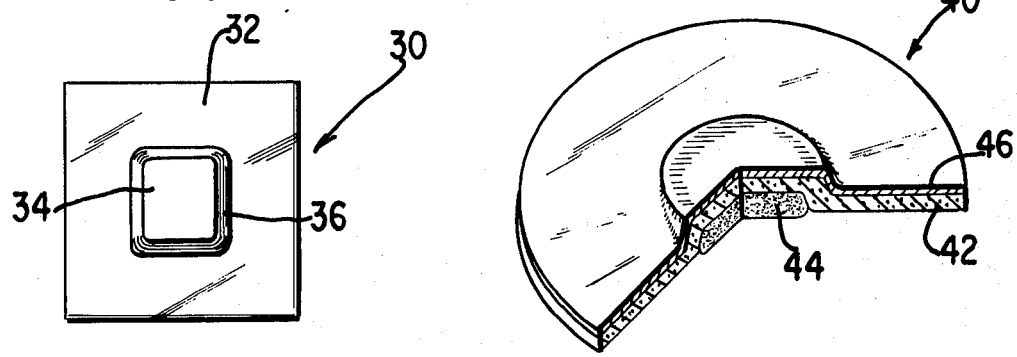
FIG.3
FIG.4

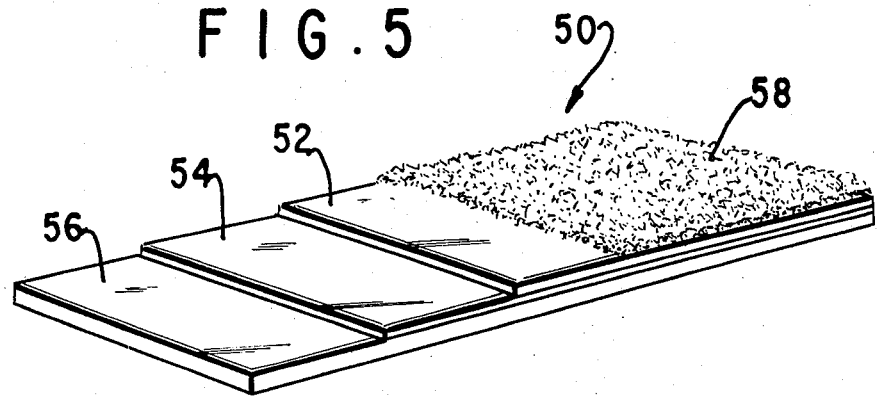
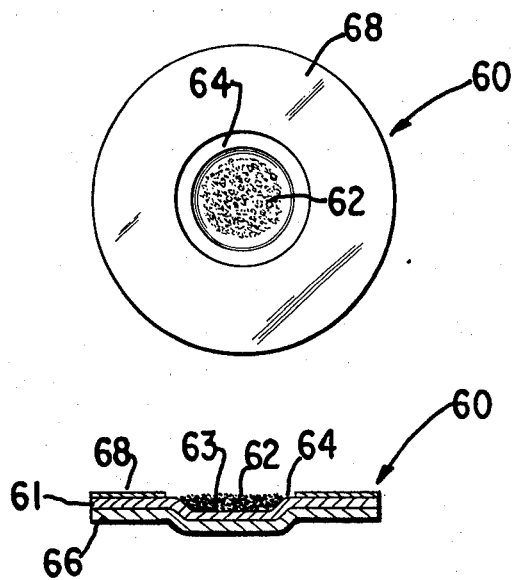
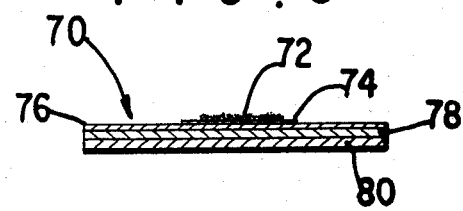

DOSAGE FORM

STATEMENT OF INVENTION

This invention is directed to dosage forms containing an active ingredient. More particularly, the invention relates to dosage forms which may be applied to moist body surfaces and remain adhering to such surfaces for an extended period. The invention is especially directed to dosage forms which are useful for securing a quickly releasable dose of active ingredient to the interior surfaces of the mouth.

It is a feature of the present invention to provide a dosage form for maintaining a medicament either in a fast release or a slow release form on the interior surfaces of the mouth while isolating the medicament from oral secretions. Thus one dosage form is provided for presenting a loading dose to a limited area of the oral mucosa and a second dosage form is provided for presenting a maintenance dose.

It is another feature of the present invention to provide a dosage form and method of administration in which the active ingredient enters the body only through the mucosa.

It is still another feature of the present invention to provide a dosage form in which the active ingredient is prevented from entering the gastrointestinal tract during administration.

The invention may be embodied in a dosage form enabling a layer of drug to be maintained in direct and intimate contact with a limited area of the oral mucosa for extended periods of time while isolating the layer of drug from the rest of the oral cavity, thereby preventing the drug from being influenced or carried away by the normal secretions of the oral cavity, and allowing essentially normal functioning of the oral cavity during the maintenance of the drug layer in contact with said mucosa.

Such a dosage form can be a buccal tape comprising a preshaped, water-insoluble, support member having a concave recess defined therein, a moisture-activated adhesive precursor applied to the side of the support member having the concave recess therein, and adapted to be activated by water, and a medicament supported in the recess by the adhesive. More than one recess can be provided in the support member, for example, for simultaneous administration of two drugs.

Advantageously the concave recess defined in the support member is shaped by thermoforming and the top surface of the medicament supported in the recess is coplanar with the top surface comprising the exposed margin of adhesive.

In another embodiment, the dosage form can be a buccal tape comprising a preshaped, water-insoluble, support member having applied to one surface thereof a moisture-impervious layer, having applied to at least the outer periphery of the exposed surface of the moisture-impervious layer a moisture activated adhesive precursor layer, and having applied to the central portion of the exposed surface of the impervious layer a medicament layer.

Advantageously the medicament layer is coplanar with the adhesive layer and can be supported in a concave recess shaped in the support member.

In the method of medication employing the dosage forms of this invention containing systemically active drugs, the dosage form is applied to the inside of the oral cavity such that the drug is exposed to a relatively small area of the oral mucosa while isolating the drug from the remainder of the oral cavity, maintaining the exposure of the drug to the relatively small area of the oral mucosa until substantially quantitative penetration of the drug through the mucosa is accomplished, and removing and discarding the drug depleted dosage form.

DISCUSSION OF PRIOR ART

The desirability of buccal delivery of drugs has long been recognized, the most notable advantage being the avoidance of "first pass" metabolism in the intestinal tract or in the liver. Various buccal and sublingual tablets are in current use. However, no prior art tape exposes, yet isolates the drug according to this invention. The inventive concept thus resides in the structural arrangement of the various parts of the tape, as well as the substances that are incorporated in those parts. The combination of all of the parts makes the buccal tape of this invention a practical method of dosage.

Thus U.S. Pat. No. 3,536,809, issued Oct. 27, 1970, describes a medication method wherein the drug is incorporated in a buccal tape which is in a releasable form from all surfaces.

U.S. Pat. No. 3,699,963, issued Oct. 24, 1972, describes buccal administration by means of a steady and even metering of the drug to the treatment surface, over a long period of time. To this end, a diffusion barrier is interposed between the drug and the surface.

U.S. Pat. No. 3,339,546, issued Sept. 5, 1967, describes bandages for the oral cavity which may incorporate medicaments primarily for topical and not systemic administration.

These patents are typical of the prior art and do not disclose the method of administration and the dosage forms of this invention which provide for relatively quantitative administration of a drug through a limited area of the oral mucosa while isolating the drug from the remainer of the oral environment such that high drug blood levels are rapidly achieved and maintained in a manner analogous to drug administration by parenteral injection. Indeed, high blood levels of isosorbide dinitrate have been achieved within fifteen minutes with the dosage forms of this invention and maintained for several hours during quantitative penetration of the drug through the oral mucosa.

DETAILED DESCRIPTION OF THE INVENTION

The dosage forms of the present invention are further described in conjunction with the drawings in which:

FIG. 1 is a cross section view of a buccal tape utilizing the features of the present invention;

FIG. 2 is a bottom view of the buccal tape of FIG. 1 with the protective layer removed;

FIG. 3 is a top view of an alternate embodiment showing a square-shaped tape;

FIG. 4 is a perspective view, partly in section, of another alternate embodiment showing a generally round tape;

FIG. 5 is a partial perspective view of an alternate embodiment of a buccal tape of the present invention utilizing an internal impervious layer;

FIG. 6 is a bottom view of another embodiment of the present invention;

FIG. 7 is a sectional view of the embodiment of FIG. 6;

FIG. 8 is a sectional view of still another embodiment of a buccal tape of the present invention.

The objects of the present invention may be achieved with a buccal tape 10 comprised of support member 12 which has a concave recess 14 formed in it. An adhesive layer 16 is applied to the concave side 18 of the support number 12. A medicament 20 is supported in the recess 14 by the adhesive. The medicament 20 has active ingredient 22 distributed through it. A protective member 24 is connected to the adhesive layer 16 and covers the adhesive layer and the medicament 20 during shipping and storage. The protective member 24 is removed prior to use.

As may be seen in the bottom view, FIG. 2, the described embodiment is generally rectangular. The recess 14 is also generally rectangular and is surrounded by the adhesive layer 16.

As may be seen in FIG. 1 it is preferred that the surface 26 of the medicament lie in substantially the same plane as the surface of the adhesive layer 16.

An alternate embodiment is shown in FIG. 3 where a generally square tape 30 is made up of an adhesive layer 32 connected to a support member (not shown) and having at its center a medicament 34 supported by the adhesive in a recess 36.

It is to be understood that the cross section through either FIG. 3 or FIG. 4 would be substantially the same as FIG. 1.

Another alternate embodiment is shown in FIG. 4. There a buccal tape 40 is shown in a generally round embodiment and is comprised of an adhesive layer 42 applied to a support member 46. A medicament 44 is contained in a recess 48 and supported by the adhesive layer 42.

The support member of the present invention can be any suitable material which is approved for use in food or drugs. A support member can be an inert film composed of ethylcellulose, ethylmethylcellulose, cellulose acetate phthalate or resins usable in chewing gum base.

The support member can also include a plasticizer to render it flexible. The support member can include an additive to increase its hydrophilicity.

In industrial practice such a support member would be identified as an inert film which could be prepared by melt extrusion or casting from a solvent.

The moisture impervious layer can be any of the rubbers, for example, preferably in an uncured tacky form, such as natural rubber, silicone rubber, acrylonitrite rubber, polyurethane rubber, polyisobutylene rubber, polyisobutylene-isoprene rubber, and the like.

The adhesive layer can be selected from a series of water-soluble polmers such as hydroxypropylcellulose, carboxymethylcellulose, dextran, guar gum, polyvinyl pyrrolidone and the like. The adhesive compositions described in U.S. Pat. No. 3,339,546, which consist of finely powdered hydrocolloids are particularly suited for this purpose. These hydrocolloids develop their adhesiveness toward wet surfaces only after they are hydrated. The prior art binder, polyisobutylene, however, does not adhere to wet surfaces, and being insoluble in water, it gets in the way of the moisture as it tries to reach the hydrocolloid. The binder of the present invention is therefore a viscous solution of polyvinylpyrrolidone in liquid polyethylene glycol or glycerol. The binder of the present invention is water soluble, and offers no hindrance to the passage of moisture. Moreover, the present binder is effective at 25 percent by weight, as opposed to the prior art 58–60 percent by weight, allowing a higher content of the adhesive hydrocolloid, resulting in greater adhesion.

The adhesive is activated by water, for instance by the water in saliva, and is then able to adhere to an area of mucosa for up to 8 hours.

The medicament is placed onto the adhesive coated side of the support member. In the central portion, the thickness of the medicament varies according to the dose and the desired release rate of the drug. For the rapid release of a small amount of drug, a thin layer of the pure drug deposited directly onto the adhesive may be satisfactory. For a slower, or substained release, a bulkier matrix in which the drug is dispersed is required. The matrix or binder, for the drug may be any of the substances known to be used for such purposes and also any semisolids melting at body temperature, such as gelled aqueous solutions or cocoa butter dispersions. The matrix need not be sturdy and self supporting because the support member provides the bulk and strength requirements for the dosage form. Thus even gelled aqueous solutions or semisolid ointments can be satisfactory matrices. A matrix in a disc or other bulky form will fit into an appropriate preformed depression in the support member.

As opposed to a matrix, which slows the penetration of the drug by interposition of a diffusion barrier, adjuvants can be employed which by a chemical influence regulate drug penetration through the mucosa. For example, buffers can be included which control the pH in the isolated environment of the in-place dosage form at a level optimal for drug absorption. Such adjuvants include polymeric cations, quarternary ammonium compounds, nonionic surface active compounds, and the well known buffering compositions.

A protective layer to cover the mucosa contacting surface until the dosage form is ready to be used is applied over the outside of the adhesive. The protective layer can be coated paper or other inert film or metal foil. The protective layer is peeled off the dosage form before the latter is inserted in the mouth.

An especially advantageous related group of embodiments is shown in FIGS. 5–8. As shown schematically in FIG. 5, the buccal tape 50 of the present invention has a non-pressure-sensitive adhesive layer 52 supported on an impervious layer 54, which can be an isobutylene-isoprene copolymer, and a backing layer 56. A drug or active ingredient 58 is supported on the adhesive layer 52.

An alternate embodiment 60 is shown in FIG. 6 and 7. There the drug or active ingredient 62 with or without environment modifying adjuvants, is confined to the central part of the backing layer 66 only, which is surrounded by an adhesive margin layer 68 but has an adhesive-free area 64 devoid of drug. When the buccal tape 60 is applied onto the mucosa, the drug layer, together with the moisture trapped there, constitutes the isolated environment for the drug 62. Adjustment and control of the environment is accomplished with suitable adjuvants so as to optimize the absorption process. The adhesive layer 68 is supported on an impervious layer 67 attached to a backing layer 66.

The backing layer 66 soft, flexible and is formed of ethylcellulose plasticized with castor oil. Any stiffness in the backing layer 66 causes the tape 60 to peel off the curved surfaces of the mucosa. The backing is as soft as polyethylene and becomes even softer when in the mouth.

A water soluble binder is used for the adhesive layer 68. The adhesive is a hydrocolloid gum with a water soluble binder comprised of a mixture of polyvinyl pyrrolidone (PVP) and polyethyleneglycol having a molecular weight of about 400 (PEG 400).

The impervious middle layer 67 may be an isobutylene-isoprone copolymer and separates the backing layer 66 from the adhesive layer 68. This prevents intermigration of plasticizer or binder ingredients, initially or on aging, which would have an adverse effect on one or both of the layers.

In FIG. 8 is shown another advantageous embodiment 70 in which the active ingredient 72 is supported on an impervious layer 74 which is supported on an adhesive layer 76, which is in turn supported on a second impervious layer 78 covered by a backing layer 80. The impervious or, solvent sealant, layer 74 under the drug layer 72 prevents the drug, or the solvent vehicle in which it is applied, from penetrating into the adhesive layer. It also provides a tacky anchoring surface for the drug layer.

It is desirable to thermoform a recess 62 in the center of the buccal tape which is useful when bulky drug layers, or drug and adjuvant layers, have to be accommodated as is shown in FIG. 7. When the top of the drug layer projects appreciably above the plane of the adhesive, a stress results. The bond between the mucosa and adhesive is then subjected to a peel stress, against which its resistance is very low. The thermoformed pocket allows the drug surface to be flush with the adhesive, and so eliminates this source of premature adhesive failure. However, the buccal tape may be formed flat and without a recess as is shown in FIG. 8.

The buccal tape, as described above, performs as required in vivo. Dog studies showed that the bioavailability of certain drugs is good via this route. For dosing exclusively by the buccal route, the present tape is superior to the prior art tape, mainly because its structure and design is directed towards exposure and confinement of the drug, and, secondarily, because its adhesion to the mucosa is sufficient to insure this confinement.

EXAMPLE 1

This example describes the preparation of buccal tape dosage form. The dosage form consists of a patch of a two-layer film with a depression in its middle to accommodate the drug. The two layers of the film are: a water insoluble backing, and an adhesive layer which is activated by moisture.

To prepare the backing, a solution of 1 part ethylcellulose (Ethocel Standard, 45CP, Dow Chemical Co.) and 1 part castor oil USP in 4 parts of methylethylketone is spread on a glass plate, in a thickness such that after drying a 10 mils thick film remains. The resulting film is clear, soft and limp, but nontacky.

While still on the glass plate, the dried backing is overlaid with the adhesive casting mixture. This mixture consists of finely ground karaya gum, a binder substance, and a volatile diluent for spreadability. The mixture consists of powdered gum karaya (superfine XXXX, Meer Corp.), 65% of the final dry weight, polyvinyl pyrrolidone (molecular weight about 40,000, pharmaceutical grade), 17.5% of dry weight, glycerol, 17.5% of dry weight, dispersed and/or dissolved in absolute ethanol, about 55% of dry weight. The adhesive mixture is cast in such thickness that after drying the adhesive layer is 4–5 mils thick.

The dried two-layer film is removed from the glass plate. It is flat and limp, but self-supporting. The adhesive side is grainy, semi-opaque, and very slightly tacky. It is cut into three-quarter inch diameter circular patches. A circular depression, about 3/16 inch diameter, and about 0.04 inches deep is formed in its middle by vacuum thermoforming. For this, the patch is placed, with its adhesive side up, on a vacuum chamber device, equipped with a suitable hole and backstop. After heating the patch moderately from above with an infrared heater, the vacuum is applied briefly, to create the desired depression, which becomes permanent as the patch cools.

For endurance testing, indicator wafers are inserted in the depressions. These wafers are made from usual pharmaceutical ingredients. In the actual dosage form they could consist of, or contain, any suitable drug. For testing in vitro, the wafer contains a dye, such as methylene blue, as an indicator. The patch is moistened, then stuck onto a vertical sheet of dialysis membrane, immersed in a 37° C water bath, and flexed constantly by means of a rotating eccentric shaft. Patches typically endured for 4 hours in this test, then the dye started to leak out. For testing in the mouth, the wafer is mint candy. The patch is inserted in the moutn and pressed briefly against the soft mucosa of the inside cheek, or of the inside lower or upper lip. In spite of normal mouth movements and speech, the patches endure for more than an hour, then start to leak, as signaled by mint taste. Patches stuck to the hard palate of the roof of the mouth endure much longer, up to 5 hours.

EXAMPLE II

This example describes an alternate method of preparing buccal tapes and the method of incorporating the active ingredient.

Step 1

The backing layer is formed by spreading a solution of ethylcellulose (Ethocel Standard, 45 cp, Dow Chem. Co.), 1 part, and castor oil U.S.P., 1 part, in 4 parts of methyl ethyl ketone onto a glass plate, and allowing the solvent to evaporate. The backing layer is about 10 mils thick.

Step 2

The middle layer is deposited on top of the backing, by spreading a solution of 1 part of Butyl Rubber 007 (Exxon Chemical Co.) in 3 parts of n-heptane over it, and allowing the solvent to evaporate. The middle layer is from 0.5 to 1 mils thick.

Step 3

The adhesive layer is deposited on top of the middle layer, by spreading a slurry over it. This slurry is composed of 10 parts of karaya gum, superfine XXXX (Meer Corp.) which is slurried, shortly before the spreading operation, into 10.5 parts of a binder solution. The binder solution contains 15.85 percent by weight each of polyethylene glycol (PEG 400), and polyvinylpyrrolidone (PVP C–30), in absolute ethanol. After spreading, and evaporation of solvent, the semiopaque grainy and non-tacky adhesive layer is 3 to 3.5 mils thick. Its composition by weight is 75 percent karaya gum, 12.5 percent PEG 400 and PVP C–30.

The buccal tape laminate is now complete. The steps below describe the laboratory process for loading the drug isosorbide dinitrate onto the buccal tapes.

Step 4

A solvent sealant layer is deposited on top of the adhesive layer, to cover a circular portion around the center of the tape, about 5/16 inch in diameter. For this, a 0.02 ml. drop of a 7.5 percent solution of Butyl Rubber (007) in n-heptane is applied to the desired area, and the solvent is allowed to evaporate.

Step 5

The laminate is cut into one inch diameter circles, with the solvent sealant layer in their center.

Step 6

The crystal seeding agent is applied. This is a slurry of colloidal silica (Cabosil), 1 part in 75 parts of acetone. The slurry is applied to the center in portions, the volume of each portion being such that the slurry spreads in a circle of about ¼ inch diameter, and each portion is allowed to dry. A total of 0.1 ml. slurry is so applied. The silica left behind causes the drug to crystallize uniformly and evenly in the next step.

Step 7

A solution of isosorbide dinitrate in acetone, at a concentration of 40mg./ml., is metered onto the center in portions of 0.0025 ml. The solvent is allowed to evaporate afer each portion. Five portions are so applied, for a total loading of 0.5 mg. drug per tape. This completes the loading of the tape. The drug is in the form of a thin layer of crystals, distributed evenly on the surface of the center part of the tape.

The inside of the cheek, near the molar teeth, is the most favored area of application. The insides of the lips or the hard palate of the roof of the mouth are other possible areas. In using a dose form as described, position a buccal tape on the outstretched thumb, shiny side of tape down. Do not lick or pre-moisten the tape. Open mouth about one inch. With the forefinger of the other hand hooked into the corner of the mouth, pull it out slightly, to open a passage to the inner cheek. With the buccal tape riding on the thumb, insert it in the mouth and flatten it against the inner wall. The tape should be held in place, with thumb or with the tongue, for a few seconds. Activated by the trapped saliva, the adhesive will stick the tape to the mouth during this time. While this occurs, the position of the tape can still be changed slightly, by sliding it sideways. If the tape is peeled off the mucosal surface, however, it will not stick again when reapplied.

A properly applied buccal tape feels smooth and flat against the mucosal surface, with no wrinkles, when felt with the tongue, whether the mouth is open or closed. The position of the tape should be such that in normal mouth movement the teeth should not catch, or hook into, the edge of the tape. If not wrinkled, or peeled off by the teeth, the tape will maintain the drug against the mucosa without leaking for at least an hour, while allowing normal mouth movements and speech, and even the intake of fluids.

For removal, the edge of the tape is grasped between thumb and forefinger, then peeled off the mucosal surface. Some of the adhesive layer may stay behind, and can be removed by rinsing the mouth with water. The entire buccal tape is made of materials sanctioned as food additives, and is presumably harmless when swallowed.

Typical drugs which can be administered by means of this invention are, for example, peptides such as the LH-FSH releasing hormone, somatostatin, pentagastrin, oxytocin, insulin and related compounds, isosorbide-2-mononitrate, isosorbide dinitrate, pentaerythritol nitrates, nitroglycerin and the like, prostaglandins and prostaglandin analogues, major and minor tranquilizers, antidepressants, cardiotonics, testosterone and other androgens and derivatives, progesterone and other progestins and derivatives, natural estrogens and derivatives, ergot alkaloids and derivatives, colchicine, and propranolol and other anti-adrenergics. Further typical drugs are isoproterenol, phenylephrine and other adrenergics; hydrocortisone, prednisone, triamcinolone and other adrenocorticoids; acetanimophen, codeine, propoxyphene and other analgesics; antidiarrheals; apomorphine, atropine, morphine and other alkaloids; buclizine, cyclizine, prochlorperazine and other antiemetics; hydralazine, methyldopa and other antihypertensives; sedatives and hypnotics; enzymes; antibacterials, antimicrobials; nutritional agents; heparin and other anticoagulants.

Preliminary experiments in dogs indicate that propranolol applied either as the free base or the hydrochloride salt rapidly penetrated the oral mucosa. The blood levels obtained after 15 minutes were comparable to those observed after intravenous (IV) administration. However, most importantly, a low level of metabolism was observed in 2 out of 3 dogs. Extensive liver metabolism, large doses, or interpatient variation experienced in current therapy with this drug may be reduced or better controlled via buccal tape administration. More efficient drug handling could then allow (1) reduction in drug administered, (2) reduction in side effects, and (3) evaluation of action in new or specific therapeutic indications. Possibly the metabolites of propanolol can be isolated, identified and related to specific therapeutic activity. These too could be administered buccally if necessary or advantageous.

Administration of isosorbide dinitrate to dogs via the buccal tape gave rapid significant levels of the intact drug. The levels of the mononitrate metabolites initially were much lower than those observable after oral administration. Availability of drug from the buccal tape could be controlled for specific purposes. The rapid availability of the diester offers an opportunity to compare isosorbide dinitrate to nitroglycerin in acute anginal episodes.

We claim:
1. A buccal dosage form for buccal administration of a buccally effective medicament comprising:
   a. a preshaped, planar, water-insoluble support member comprised of an inert flexible film;
   b. a concave recess defined in a portion of one surface of said support member further defining a planar margin of the support member surface surrounding the concave recess,
   c. a moisture-activated adhesive precurser comprised of a hydrocolloid admixed with polyvinylpyrrolidone applied to at least the planar margin of the support member surface surrounding the concave recess.
   d. a medicament effective buccally supported in said concave recess, the top surface of said medicament being below or coplanar with the margin of said support member surface surrounding the concave recess.

2. A buccal dosage form for buccal administration of a buccally effective medicament comprising:
   a. a preshaped, planar water-insoluble support member comprised of a film of ethylcellulose plasticized with castor oil;
   b. a concave recess defined in a portion of one surface of said support member further defining a planar margin of the surface of said support member surrounding the concave recess,
   c. a moisture-impervious layer comprised of an isobutyleneisoprene copolymer applied to the side of said support member wherein the concave recess is defined;
   d. a moisture activated adhesive precursor comprised of finely powdered Karaya gum in a viscous solution of polyvinylpyrrolidone in polyethylene glycol applied to at least the planar margin of the support member surface surrounding the concave recess;
   e. a medicament effective buccally supported in said concave recess, the top surface of said medicament being below or coplanar with the margin of the surface of said support member surrounding the concave surface.

* * * * *